(12) United States Patent
Nagar et al.

(10) Patent No.: US 10,842,943 B2
(45) Date of Patent: Nov. 24, 2020

(54) DRUG DISPENSING-TRACKING DEVICE, SYSTEM AND METHOD

(71) Applicant: Insuline Medical Ltd., Jerusalem (IL)

(72) Inventors: Ron Nagar, Tel Aviv (IL); Gabriel Bitton, Jerusalem (IL); Moshe Fadlun, Rishon LeZion (IL)

(73) Assignee: INSULINE MEDICAL LTD., Jerusalem (IL)

( * ) Notice: Subject to any disclaimer, the term of this patent is extended or adjusted under 35 U.S.C. 154(b) by 0 days.

(21) Appl. No.: 16/289,496

(22) Filed: Feb. 28, 2019

(65) Prior Publication Data

US 2019/0192779 A1 Jun. 27, 2019

Related U.S. Application Data

(63) Continuation of application No. 14/438,177, filed as application No. PCT/IL2013/050857 on Oct. 22, 2013, now abandoned.

(Continued)

(51) Int. Cl.
*A61M 5/315* (2006.01)
*B01L 3/02* (2006.01)
(Continued)

(52) U.S. Cl.
CPC ...... *A61M 5/31535* (2013.01); *A61M 5/3202* (2013.01); *A61M 5/50* (2013.01);
(Continued)

(58) Field of Classification Search
CPC .. A61M 5/31535; A61M 5/3202; A61M 5/50; A61M 2205/582; A61M 2205/581; A61M 2205/52; A61M 2205/50; A61M 2205/3561; A61M 2205/583; A61M 2205/3306; A61M 2205/3327; A61M 2205/3569; A61M 2205/18; G06F 19/3481; G08B 3/10; B01L 3/0293; B01L 2300/0627; B01L 2300/022;
(Continued)

(56) References Cited

U.S. PATENT DOCUMENTS 5,536,249 A * 7/1996 Castellano ........ A61M 5/31553
604/65
2008/0312604 A1* 12/2008 Boesen ............. A61M 5/31568
604/207

(Continued)

*Primary Examiner* — Brian Wilson

(57) ABSTRACT

Embodiments of the present disclosure present systems, methods and devices related to the tracking of drugs injected by injection devices. For example, in some embodiments, a drug dispensing-tracking device for use in combination with a drug-injection device is provided, where the device comprises a sleeve configured to connect with at least one mechanical feature provided on the injection device, a battery, at least one sensor, an electrical circuit for analog or digital short range communication, and a transmission element. In some embodiments, for each injection, the sensor is configured to automatically detect at least one of an auditory signal, movement, and optical signal, and an auditory signal is generated by at least one of the setting of the injection device for dispensing a drug, the dispensing action of the injection device, and the flow of the drug out of the injection device.

20 Claims, 11 Drawing Sheets

Related U.S. Application Data

(60) Provisional application No. 61/762,914, filed on Feb. 10, 2013, provisional application No. 61/727,709, filed on Nov. 18, 2012, provisional application No. 61/717,292, filed on Oct. 23, 2012.

(51) Int. Cl.
  | | |
  |---|---|
  | *A61M 5/32* | (2006.01) |
  | *A61M 5/50* | (2006.01) |
  | *G06F 19/00* | (2018.01) |
  | *G08B 3/10* | (2006.01) |

(52) U.S. Cl.
  CPC ........ *B01L 3/0293* (2013.01); *G06F 19/3481* (2013.01); *G08B 3/10* (2013.01); *A61M 2205/18* (2013.01); *A61M 2205/3306* (2013.01); *A61M 2205/3327* (2013.01); *A61M 2205/3561* (2013.01); *A61M 2205/3569* (2013.01); *A61M 2205/50* (2013.01); *A61M 2205/52* (2013.01); *A61M 2205/581* (2013.01); *A61M 2205/582* (2013.01); *A61M 2205/583* (2013.01); *B01L 2200/087* (2013.01); *B01L 2300/022* (2013.01); *B01L 2300/023* (2013.01); *B01L 2300/0627* (2013.01); *B01L 2300/0672* (2013.01)

(58) Field of Classification Search
  CPC ....... B01L 2300/0672; B01L 2300/023; B01L 2200/087
  See application file for complete search history.

(56) References Cited

U.S. PATENT DOCUMENTS

| | | | |
|---|---|---|---|
| 2009/0256703 A1* | 10/2009 | Bolton | G07C 13/00 340/540 |
| 2010/0069730 A1* | 3/2010 | Bergstrom | G06Q 50/24 600/365 |
| 2012/0022458 A1* | 1/2012 | Oh | A61M 5/31525 604/189 |
| 2012/0036018 A1* | 2/2012 | Feliciano | G06Q 50/01 705/14.66 |
| 2014/0194826 A1* | 7/2014 | Nielsen | A61M 5/24 604/189 |
| 2014/0207080 A1* | 7/2014 | Allerdings | A61M 5/168 604/207 |
| 2014/0354998 A1* | 12/2014 | Bock | A61M 5/31528 356/445 |
| 2015/0032059 A1* | 1/2015 | Allerdings | A61M 5/31525 604/189 |

\* cited by examiner

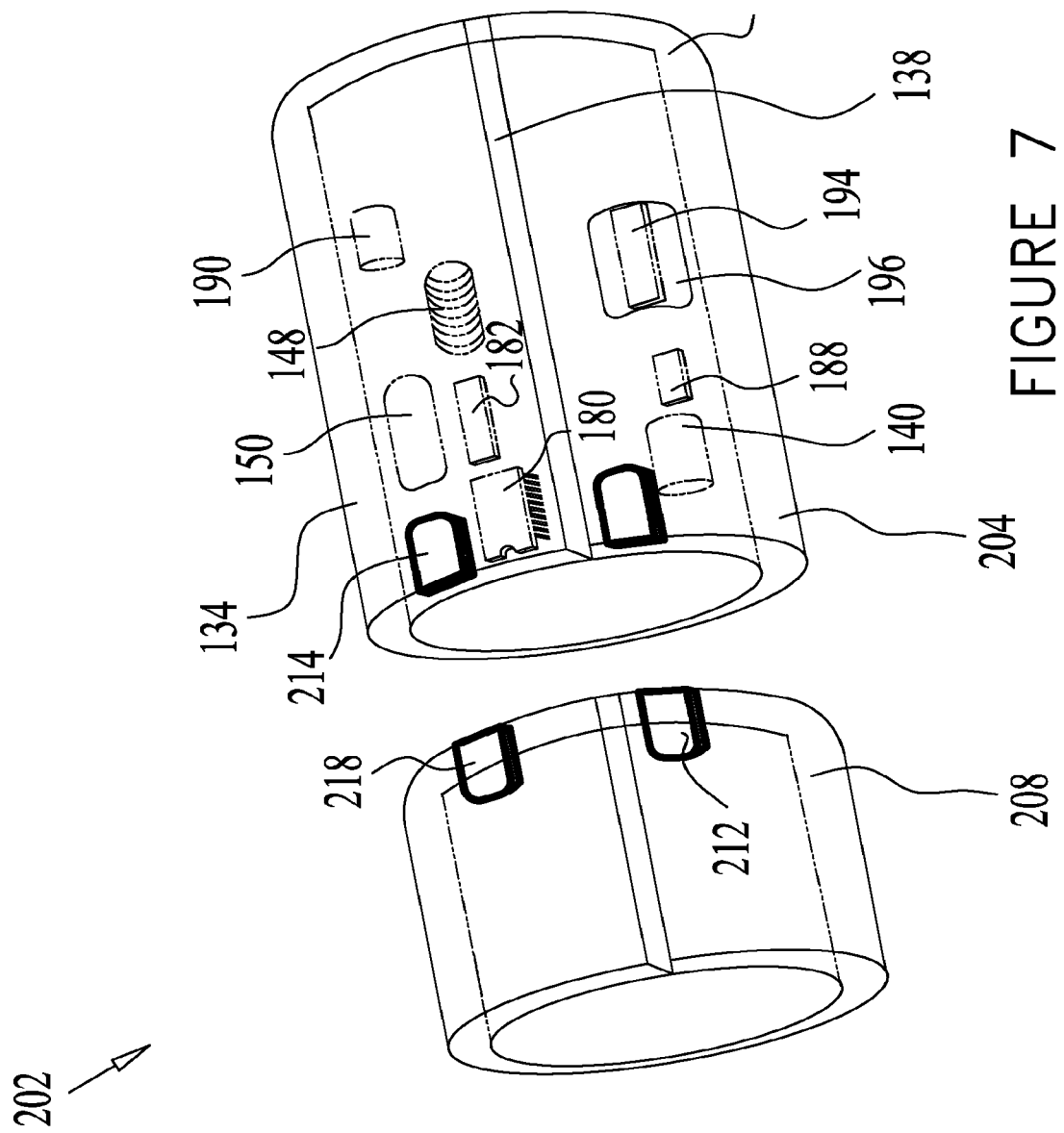

DRUG DISPENSING-TRACKING DEVICE, SYSTEM AND METHOD

CROSS REFERENCE TO RELATED APPLICATIONS

This application is a continuation application of U.S. patent application Ser. No. 14/438,177, filed Apr. 23, 2015, and entitled "Drug Dispensing-Tracking Device, System and Method," which claims priority to International Patent Application No. PCT/IL2013/050857, filed Oct. 22, 2013, and entitled "Drug Dispensing-Tracking Device, System and Method," which in turn claims priority to U.S. Provisional Patent Application No. 61/717,292, filed Oct. 23, 2012, and entitled "Device System and Method for Drug Injectors" U.S. Provisional Patent Application No. 61/727,709, filed Nov. 18, 2012, and entitled "Device System and Method for Drug Injectors," and U.S. Provisional Patent Application No. 61/762,914, filed Feb. 10, 2013, and entitled "Device System and Method for Drug Injectors." The present application incorporates herein by reference the disclosures of each of the above-referenced applications in their entireties.

TECHNICAL FIELD

Embodiments of the present disclosure generally relate to drug dispensers and particularly to drug dispensing, injecting and tracking devices, systems and corresponding methods thereof.

BACKGROUND

Various illnesses and disorders require multiple injections to control or treat a physiological condition. For example, insulin dependent diabetics are required to inject several injections of insulin, of one or more types, each day to control their blood sugar levels. In order to track the treatment diabetics are required to log each injection in a log book and report the injections, as well as their blood sugar levels, at the time of injections to their physician on each visit to the physician. The data records may be used by the physician to administrate further course of treatment. Therefore proper data recording is important to achieve improvement in treatment. Patients, such as diabetics, during the course of their daily treatment, may use more than one injection device, disposable or reusable, to inject insulin, of the same or different type while they usually use a single blood glucose meter to measure their blood glucose levels during that time.

Some blood glucose meters today are capable of logging each measurement or even real time wireless transmission of the measurement to a central database (like the TELCARE® blood glucose meter: http://telecare.com/), and there also are injection devices (e.g., injection pens) that have integrated logging functionality (e.g., amount of injected drug, time of injection, and date, such as the PENDIQ® device http://www.pendiq.com). To that end, if a diabetic is using more than one injection device to make injections, not all injection events are available in a central device (i.e., a single device) for later download at the physician office, or real time transfer to a central database. Even if the diabetic is using an injection device which is capable of recording the injection event, not all injection events are available in a central device for later download at the physician office, or real time transfer to a central database.

Therefore it is desirable to have a simple, inexpensive device and method which is capable of capturing and recording all injection events from one or more injection devices and logging them wirelessly to a central device and/or to a central database.

SUMMARY OF DISCLOSURE

Some of the devices according to the present disclosure overcome the deficiencies of the current state of the art by providing an attachment which can be affixed on any drug-injector device (e.g., a pen injector), hereinafter referred to a "drug dispensing-tracking device" or a "tracking device". The tracking device may be formed of or with a sleeve or housing configured to, for example, slide or otherwise be affixed on and/or off an injection device (the terms "sleeve" and "body" can be used interchangeably throughout the present disclosure). The sleeve can be configured to fit mechanical features on the body of the injection device so as to prevent it from detaching from the injection device or otherwise uniquely fit to a certain injection device with a specific drug. The body of the device (e.g., the sleeve) can include at least one of a battery, a sensor that can be, for example, at least one microphone, electrical circuit, a transmission element such as a transponder and optionally, a switch, A/D converter, processor, unique identifier and memory. In some embodiments, where the sensor comprises at least one microphone, the microphone may be activated with each injection, capturing (for example), the sound and vibration created when the user sets the injection device to inject the desired amount of drug. The microphone may also capture sounds at the time when the drug is injected (such sound information may be stored on the device with provided memory or otherwise immediately wirelessly transmitted to another unit for analysis). This information may be transmitted to a unit which can capture the signal, analyze it to get the data on the amount of drug that was just injected, or if the device has a memory, a processor and a unique identifier, the processor can analyze the sound information to get the information on the amount of drug that was injected, store it in the memory and transmit it to a receiving central unit (e.g. an external unit and/or central database) along with the unique identification information.

In some embodiments, the sleeve may be arranged on any injector devices of a user. Afterwards, each injection made by those injector devices can then be wirelessly transmitted to a central unit (which may be immediately after injection, or at a later time). The data transmitted to the central unit can be logged for later download to a central database, or if the central unit has cellular wireless transmission capabilities (for example, or other wireless transmission functionality), the data may be transferred in real time to a central database. Such a central unit can be any of, for example: a blood glucose meter, and a device worn on the skin of the user which may also be used to improve the kinetics of the injected drug like the INSUPAD® device of Insuline-Medical (insuline-medical.com), a cellular phone, and any other device which can be in wireless communication with each of the sleeves.

In some embodiments, the sleeve may include a switch that can be toggled between two or more states by the user, including, for example, turning the injection device on, directional indication for indicating the direction of an injection device rotation to set the amount of the injected drug and/or correction of a mistake made by the user in the amount to be injected. The sleeve may also include an element (e.g., sensor) for automatic detection of an injection event that is monitored by a processor (e.g., of the sleeve) to sense when an injection event is to be performed. Such an injection event sensor may be realized by communication between the sleeve electronics of embodiments according to the present disclosure and the electronics of a blood glucose meter and/or the electronics of a device like INSUPAD, to sense when a blood glucose measurement was taken, or when the INSUPAD (for example) was activated. Since such events come before an injection, they can be used to signal the electronics that an injection is about to be performed, and thus, the capturing electronics of the sleeve may be activated. In some embodiments, another way to realize automatic activation of the sleeve electronics can be based on removing the protective cap found on the injection device, as most injection devices include a protective cap that is removed before injection is made. Therefore, in such a case, removing the protective cap of the injection device can be used to switch "on" the electronics of the sleeve (e.g., in some embodiments, the vibrations/noise produced when removing the cap and switch on the electronics, and/or an actual switch configured to interact with the cap can be provided on the sleeve).

One or more sensors (e.g., an array of sensors) provided with the sleeve can be, for example, at least one of or any combination of a sound sensor and a vibration sensor. A sound sensor can be surrounded by or mounted in a vibration isolation material which isolates the vibration and is sensitive to the sound signal. To that end, algorithms can be implemented that use a signal from one or more sensors to improve the detection and immunity to noise.

In some embodiments of the present disclosure, a drug dispensing-tracking device for use in combination with a drug-injection device is provided, where the device comprises a sleeve configured to connect with at least one mechanical feature provided on the injection device, a battery, at least one sensor, an electrical circuit for analog or digital short range communication, and a transmission element. In some embodiments, for each injection, the sensor is configured to automatically detect at least one of an auditory signal, movement, and optical signal, and an auditory signal is generated by at least one of the setting of the injection device for dispensing a drug, the dispensing action of the injection device, and the flow of the drug out of the injection device.

In some embodiments, a method for tracking dispensing of a drug from an injection device is provided, where the method comprises providing a dispensing tracking device, the device comprising a sleeve configured to connect with at least one mechanical feature provided on the injection device, a battery, at least one sensor, and detecting at least one of an auditory signal, movement, and an optical signal generated by at least one of the setting of the injection device for dispensing a drug, the dispensing action of the injection device, and the flow of the drug out of the injection device.

In some embodiments of the present disclosure, a system for injecting and tracking a drug is provided where the system comprises a device for tracking the dispensing of a drug injected by an injection device and an external unit. The device comprises a sleeve configured to connect with at least one mechanical feature provided on the injection device, a battery, at least one sensor, a transmission element, a processor, and a memory. For each injection, the sensor is configured to automatically detect at least one of an auditory signal, movement, and optical signal generated by at least one of the setting of the injection device for dispensing a drug, the dispensing action of the injection device, and the flow of the drug out of the injection device. The external unit may also include a memory. In some embodiments, the sensor generates a second signal in response to the detected signal, the processor converts the second signal to data, and/or the data is wirelessly transmitted via the transmission element to the external unit.

One and/or another of tracking device embodiments disclosed in the present disclosure, may additionally include one or more of the following features:
  a processor and a memory;
  the sensor comprises at least one of a microphone, a vibration sensor, an accelerometer, a rotational sensor, a magnetic sensor, an electromagnetic sensor;
  the transmission element comprises a transponder, where the sensor generates a second signal in response to the detected signal, a processor converts the second signal to data, and data is wirelessly transmitted via a transponder to an external unit;
  an external unit selected from the group consisting of a glucose meter, a computer, a smartphone, a tablet, and a treatment device worn on the skin of a user to treat an injection site to improve the pharmacodynamics of the drug during a period of delivery of the drug to the user. The external unit may be configured to analyze data to determine the amount of drug injected;
  data collected by the tracking device/system (or external unit) is stored in the memory along with, for example, time information corresponding to at least one of the date and time of a respective injection. Data may further comprise an identifier of the injection device, and may be relayed via wireless or wired connection by an external unit to a central database;
  data collected by the tracking device/system may correspond to the amount of drug injected by the injection device;
  a switch for enabling the sensor for sensing, where the switch may comprise a magnetic switch. Such a switch may be positioned in, on or adjacent to a rotating element of the injection device;
  a magnetic switch which comprises a magnet and a magnetic sensor, where the magnetic sensor may comprise a magnet and sensor for detecting the magnet or the magnetic field thereof;
  a sensor arranged with a cap of an injection device configured to generate a signal in response to rotation of the cap;
  the sensor comprises a CCD configured to capture the dose information from a dose window of the injection device;
  an optical element configured with the sleeve to be arranged adjacent the dose window;
  data may be stored in the memory along with corresponding data comprising at least one of time of injection, date of injection and type of injection device;
  a switch that can be toggled between two or more states, such states may comprise at least two of: a state for turning on the device, a state indicating the direction of injection device movement as it is set by the user to the amount of the injected drug, a state indicating readjustment of an amount of drug before injection, and a state indicating the drug is to be injected;
  a switch for turning on the device located adjacent a removable cap of the injection device, and upon removal of the injection device cap, the device is switched on, and upon placing the cap back onto the injection device, the device is switched off;
  the injection device may include a cap and the sleeve of the tracking device may be configured with two sections connected together before and at the time of placement of the tracking device on the injection device, and upon removal of the cap from the injection device, the two sections are separated resulting in two separate sections. In some embodiments, each of the two sections of the sleeve may be provided with at least a portion of a pin and the at least a portion of the pin is configured to operate a switch. Separation of the two sections, in some embodiments, is such that their removal from the device results in two separate parts which are thereafter incapable of being connected together;

generation of a second signal, by the signal, in response to the detected signal, and converting the second signal to data;

wireless or wired transmission of data via a transmission element of the tracking device to an external unit;

analyzing data by at least one of the processor (e.g., of the tracking device and or an external unit) to determine the amount of drug injected by the injection device;

detecting rotation of a cap of an injection device;

imaging a dosing window of an injection device, generating image information which may be stored in a memory of the tracking device and/or transmitted via a transmission element provided with the tracking device to an external unit and/or a central database.

These and other embodiments, features, objections and advantages thereof will be even more clear with reference to the corresponding drawings for the subject application (a brief description of which is provided immediately below), and following detailed description.

BRIEF DESCRIPTION OF THE DRAWINGS

The principles and operations of the systems, apparatuses and methods according to some embodiments of the present disclosure may be better understood with reference to the drawings, and the following description. The drawings are given for illustrative purposes only and are not meant to be limiting.

FIG. 7 is a schematic illustration of a drug dispensing-tracking device shown in FIGS. 6A-6C;

DETAILED DESCRIPTION

Figure 1:
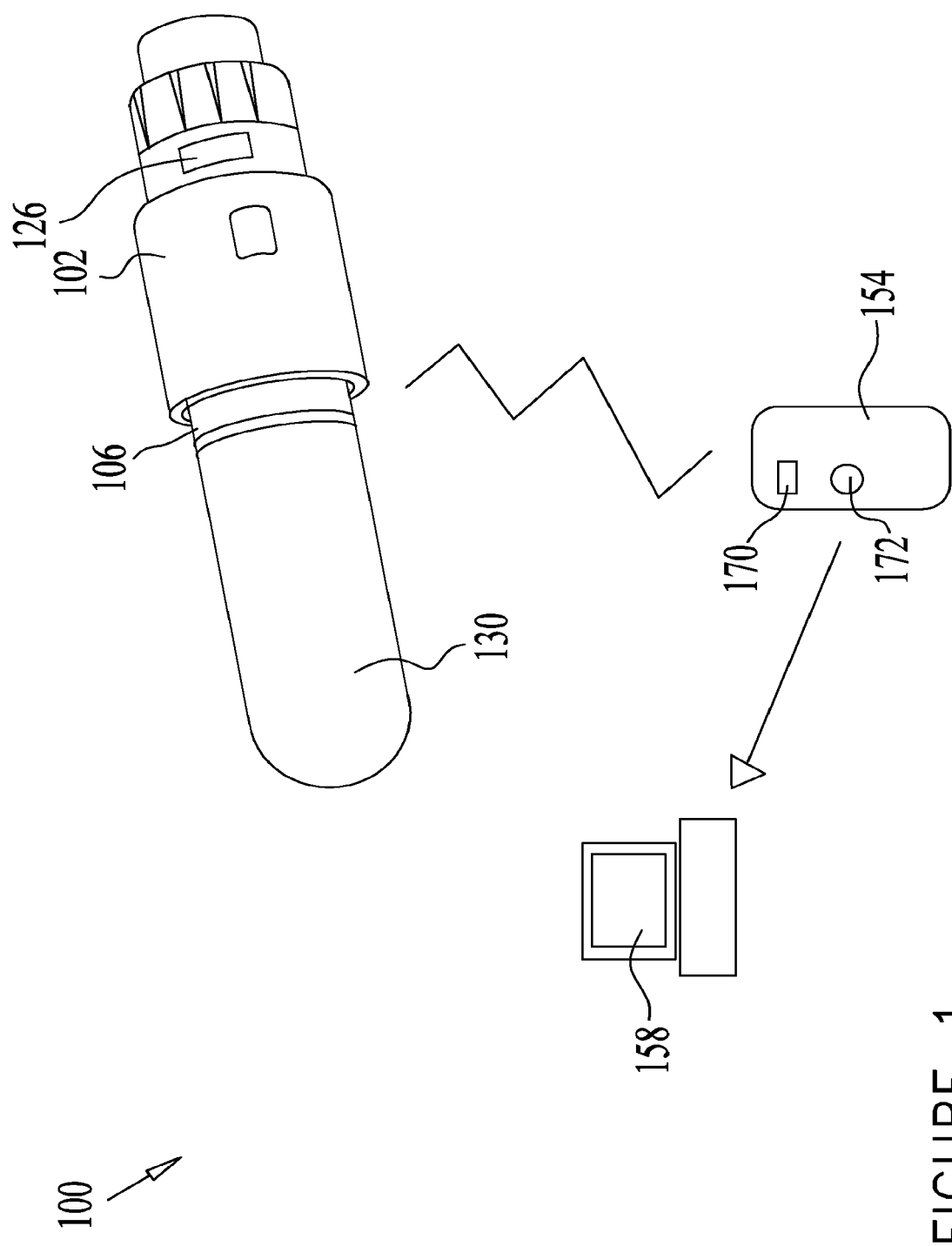
FIG. 1 is a schematic illustration of an exemplary drug dispensing-tracking system according to some embodiments of the present disclosure.
Figure 2:
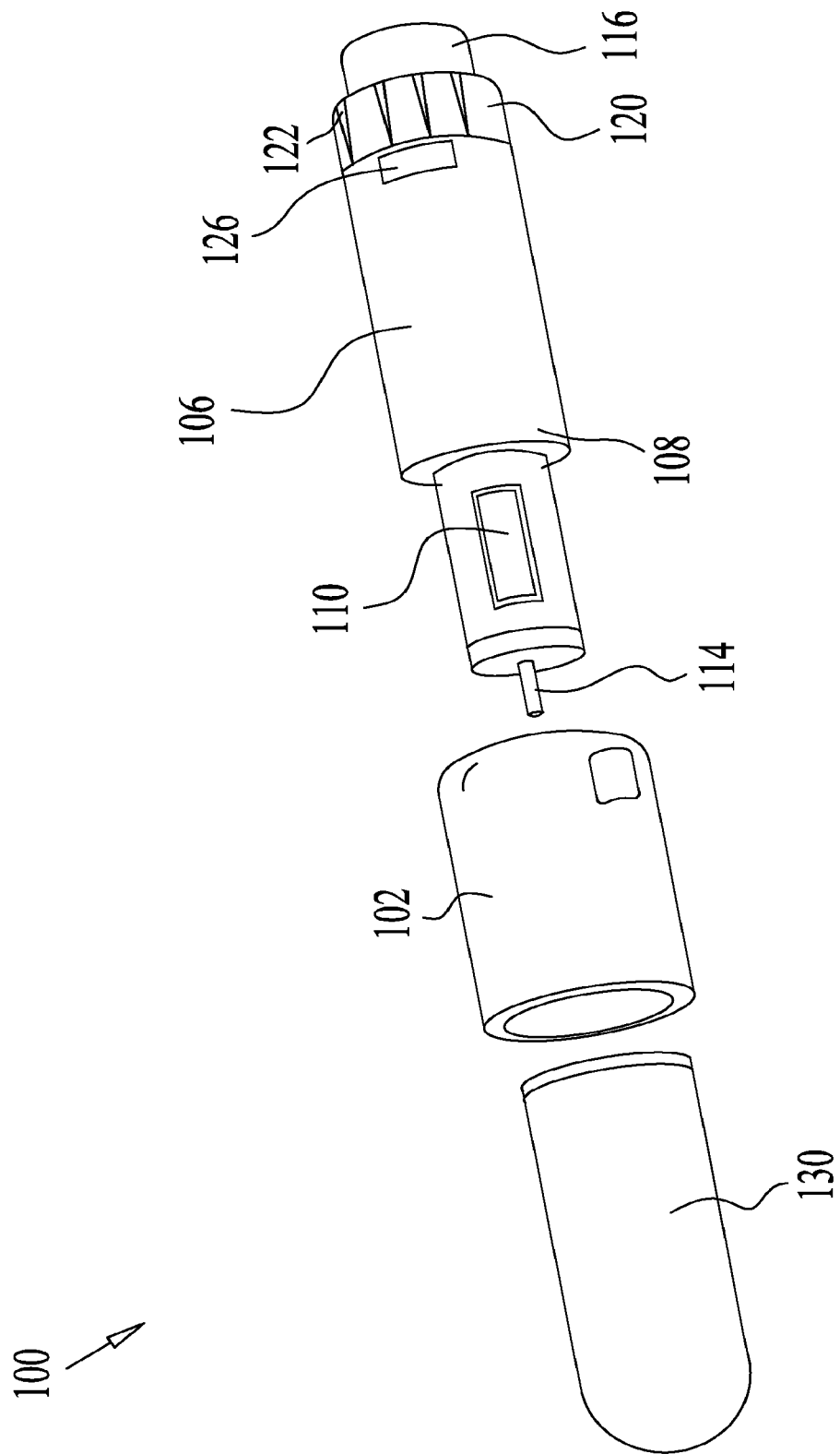
FIG. 2 is an exploded view of the drug dispensing-tracking system of FIG. 1.
Figure 3:
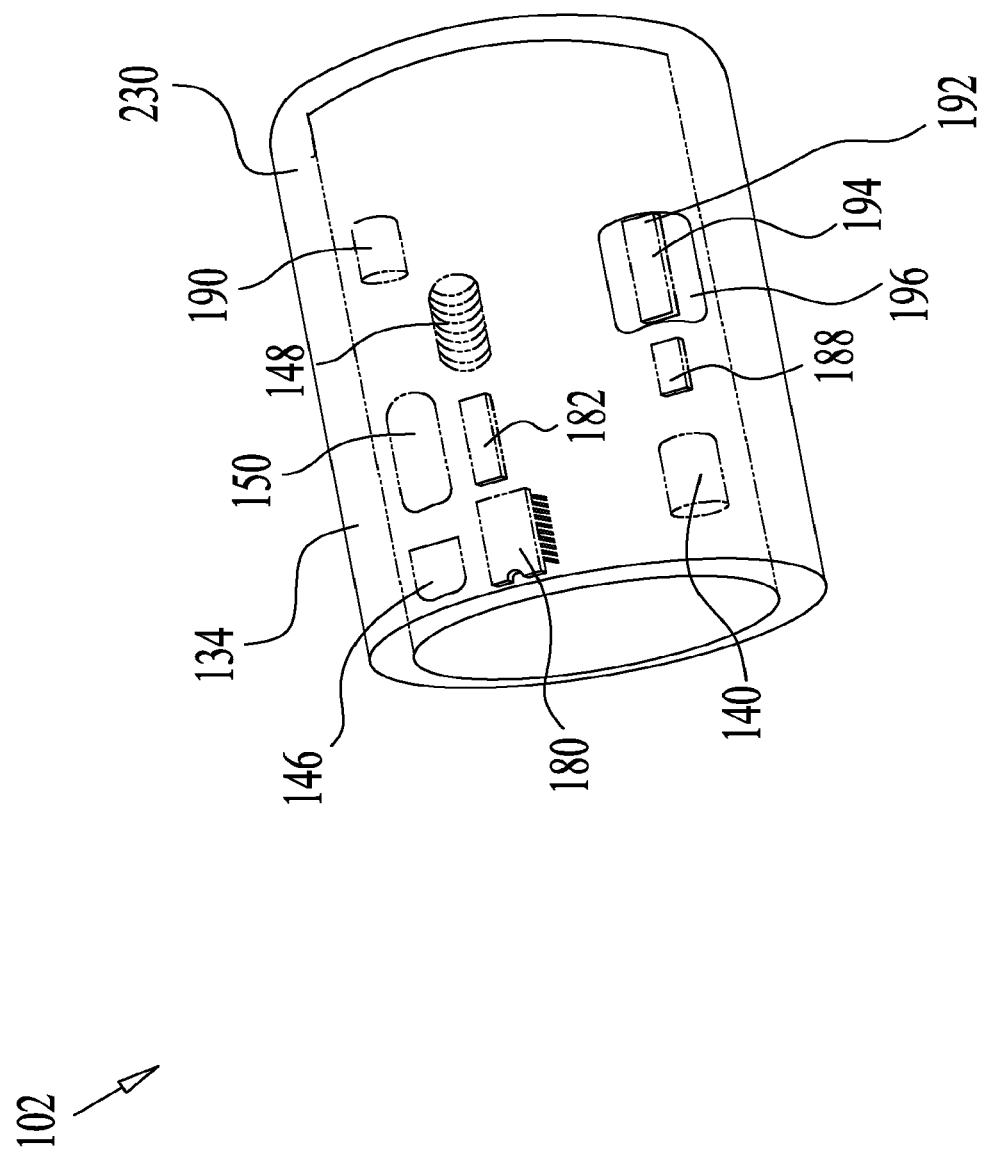
FIG. 3 is a schematic illustration of a drug dispensing-tracking device shown in FIG. 1.

FIGS. 1-4 are illustrations of an exemplary drug dispensing-tracking system 100 according to some embodiments of the present disclosures. The drug dispensing-tracking system 100 may comprise a drug dispensing-tracking device 102 used in combination with a drug-injection device 106 (or a pen injector). The injection device 106, configured for injection of a drug in a user, such as a patient, may comprise a shaft 108. The shaft 108 may be formed with a drug reservoir 110 containing a drug to be injected via a needle 114. The drug may be injected by pressing a button 116 which urges dispensing of the drug from the drug reservoir 110 into the needle 114.

Figure 9:
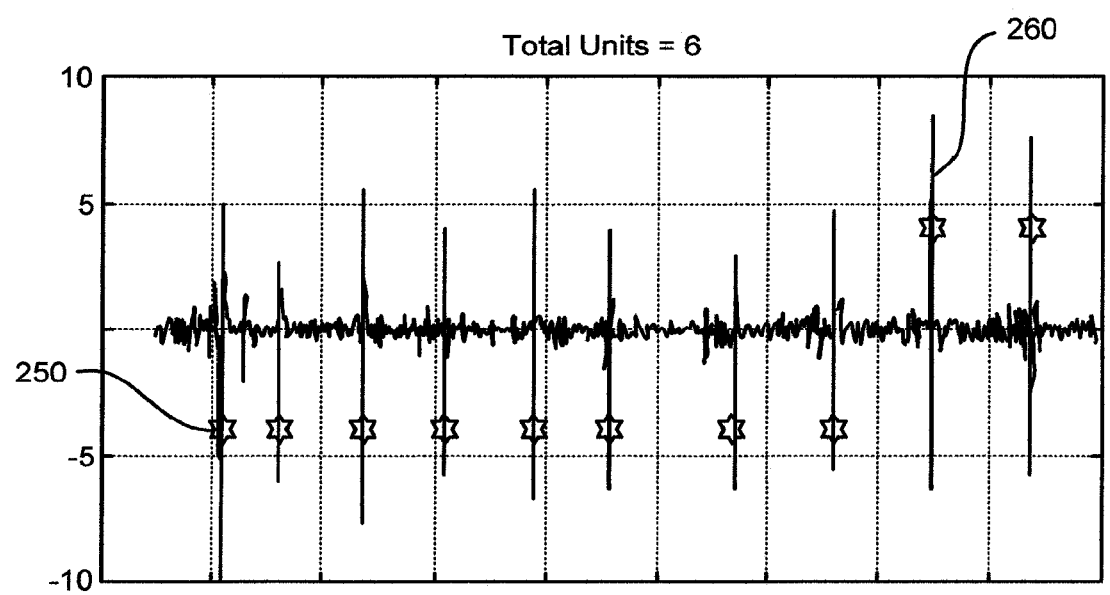
FIG. 9 is a graph illustrating a method for tracking dispensing of a drug from an injection device according to some embodiments of the present disclosure.

In some embodiments, a desired amount of injected drug may be determined by rotating a rotation knob 120. The rotation knob 120 may comprise a plurality of notches 122 or any other indicator. The rotation of the notch 122 to a first direction is performed to set the amount of drug to be dispensed from the drug reservoir 110, before the drug is injected. The rotation of the notch 122 to a second, opposite direction is performed to correct, if necessary, the amount of drug to be dispensed from the drug reservoir 110. Prior to injection, a patient may determine the desired amount of injected drug by the number of notches rotated. In some embodiments, the rotation of the knob 120 at the first or second directions may be accompanied by a clicking sound. These sounds (created by rotating the knob 120 to first or second directions) may be different when properly analyzed, as illustrated in FIG. 9.

The predetermined amount of the drug released by the rotation of a notch 122 may be different in different injection devices 106. The type of drug may be different in different injection devices 106. In some embodiments, the injection device 106 is configured for limited or even single use. Accordingly, a patient may routinely use more than one drug-injection devices 106 during the course of his daily treatment.

A display window 126 may shows the amount of injected drug. The injection device 106 may include a rotating element, such as a cap 130, which may be attached thereto in any suitable manner, such as by a snap attachment (for example).

In some embodiments, the tracking device 102 may be provided for tracking the injection of the drug and may comprise a base formed as a sleeve 134. In some embodiments, the sleeve 134 may be configured to connect with a mechanical feature of the injection device 106, removably or non-removably (i.e., permanently). In some embodiments, the tracking device may comprise a housing with one or more clamps (or clamp-like elements), for affixing (either permanently or non-permanently) to an injection device.

In some embodiments the sleeve 134 may be configured for removable or permanent connection with a mechanical feature or shape of the injection device 106, such that the shaft movement during an injection is not affected, and ease of use and accuracy of the injection device 106 may be maintained.

Figure 6A:
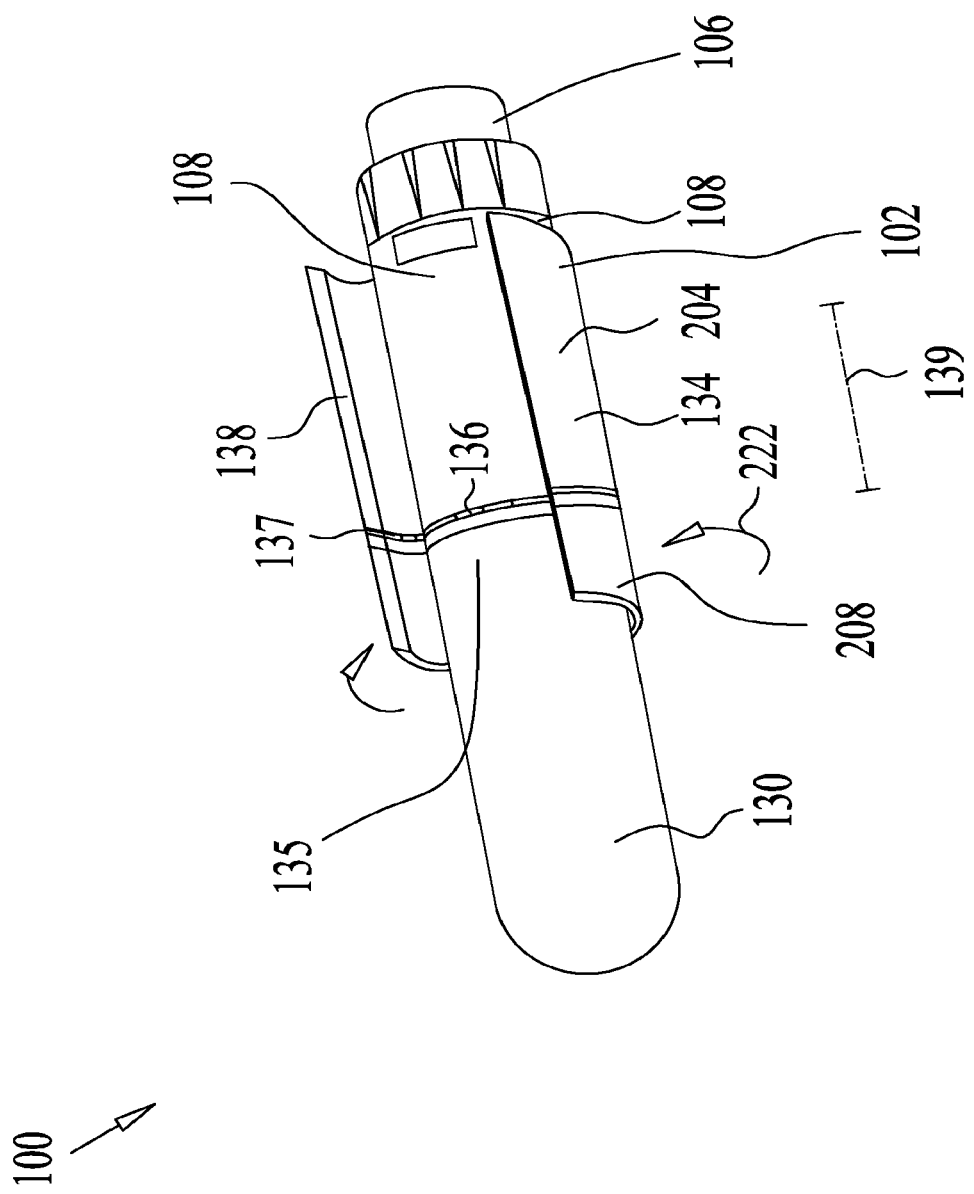
FIGS. 6A, 6B and 6C are schematic illustrations of an exemplary drug dispensing-tracking system according to some embodiments of the present disclosure, at a disassembled state (6A), at a first assembled operational state (6B) and at a second assembled operational state (6C), respectively.

In some embodiments, injection device 106 may be configured with the mechanical feature, which may comprise, for example, any structural feature, or the shape of the injection device or a feature thereof. The structural feature may include a topographical feature on an external surface 135 (FIG. 6A) of the injection device 106. The topographical feature may comprise for example, a protrusion, a dent, a notch, a recess or an aperture and may be formed in any location of the injection device 106. In some embodiments, the sleeve 134 may be formed with a mechanical feature configured to correspond with the mechanical feature of the injection device 106. In a non-limiting example as seen in FIG. 6A, the injection device 106 may be formed with a circumferential recess 136 in proximity to the interface between the cap 130 and shaft 108. The sleeve 134 may be formed with a corresponding circumferential protrusion 137 and may fit within the circumferential recess 136.

The mechanical feature of the injection device 106 may comprise any feature allowing the sleeve to connect thereto. For example, the mechanical feature may comprise a relevant dimension, such as a predetermined circumference. Accordingly, the sleeve may be formed with a corresponding circumference for fitting to the injection device 106.

In some embodiments, commercial injection devices are designed by each manufacturer usually with unique mechanical features. According to some embodiments, a sleeve 134 may be formed with mechanical features corresponding to the unique mechanical features of a selected commercial injection device and may be non-interchangeable with another sleeve formed with mechanical features corresponding to the unique mechanical features of another selected commercial injection device. Accordingly, each sleeve may be identified by its mechanical features and may be associated with a selected commercial injection device. Each type of a commercial injection device 106 may be configured to inject a specific type of drug and a specific dose. Therefore, in identifying the corresponding sleeve, the specific type of drug and a specific dose may also be identified.

Figure 6B:
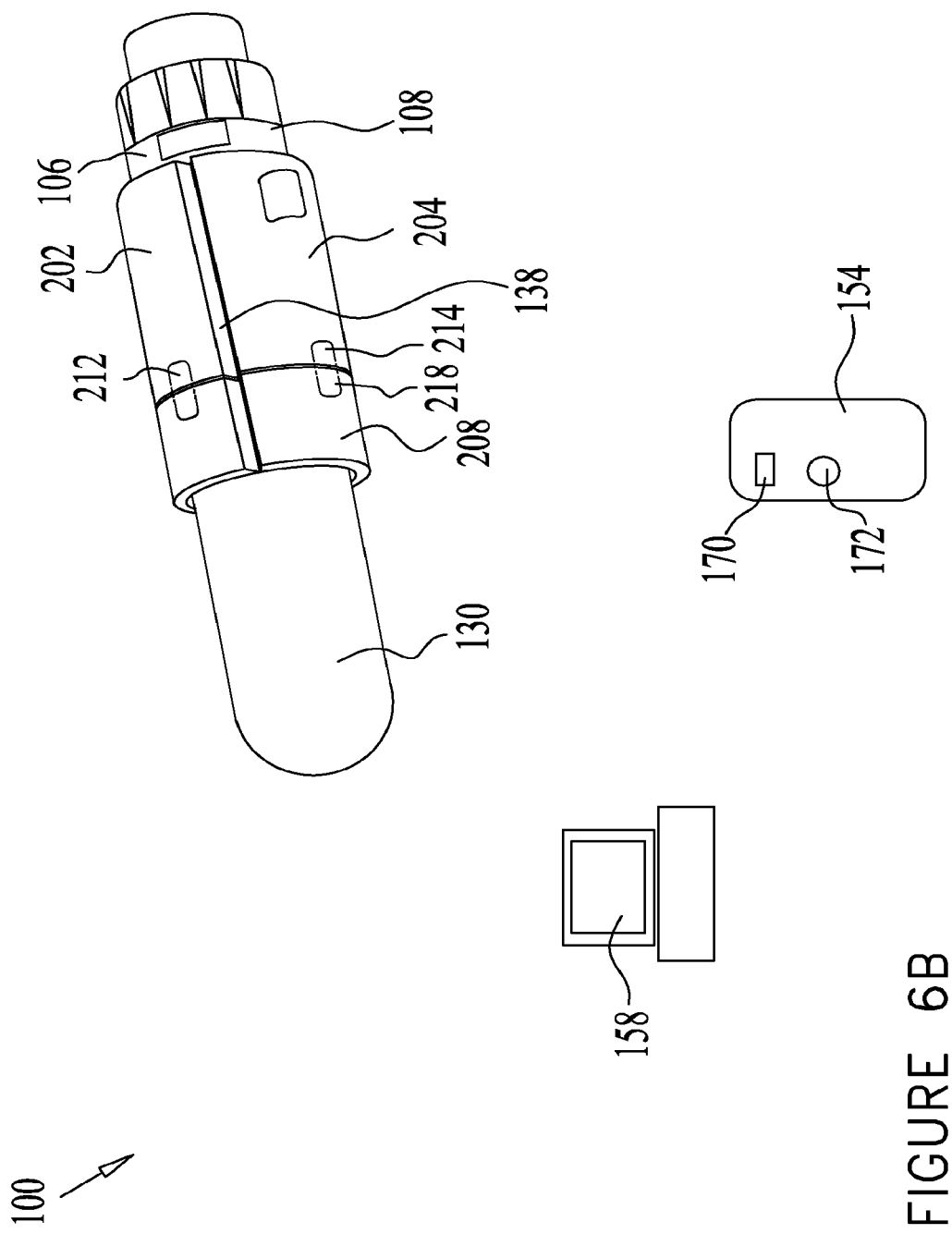

In some embodiments, the sleeve 134 may comprise a longitudinal perforation or opening 138 along a longitudinal axis 139 on at least a portion thereof. The sleeve 134 may be mounted on the tracking device 102 by opening the sleeve 134 at its perforation 138 (FIG. 6A), placing the injection device 106 within the sleeve 134 and closing the sleeve 134 over the injection device 106 (FIG. 6B).

In some embodiments, the sleeve 134 may be formed with an attachment feature for connecting to the injection device 106, such as a threaded attachment, an O-ring, a cord or a sealant or any other attachment feature securing the tracking device 102 to the injection device 106.

The tracking device 102 may comprise a sensor 140, or an array of sensors, of the same or different types or any combination of sensors, configured to detect a signal indicating an activity performed by the injection device 106. The activity performed by the injection device 106 may be, yet not limited to, any one of setting the injection device 106 for dispensing the drug, the dispensing action of the injection device 106 or the flow of the drug into a user.

In some embodiments, the signal may be an auditory signal generated by an activity performed by the injection device 106. The sensor 140 may comprise a microphone for detecting the auditory signal, such as the clicking sound generated at the rotation of the knob 120 and/or the pressing of the button 116. In some embodiments, auditory signals may include any vibration generated by setting and/or using the injection device. The microphone may comprise any suitable configuration such as an analog device including an ADMP504, ADMP521 or ADMP441-I2S. In some embodiments, the number of clicks detected by the microphone may indicate the amount of drug injected by the user. Additionally, the microphone may detect different distinguishable sounds indicating the direction of the rotation of the knob 120, which as described, may correspond to addition or removal of the drug for injection thereof.

Figure 4:
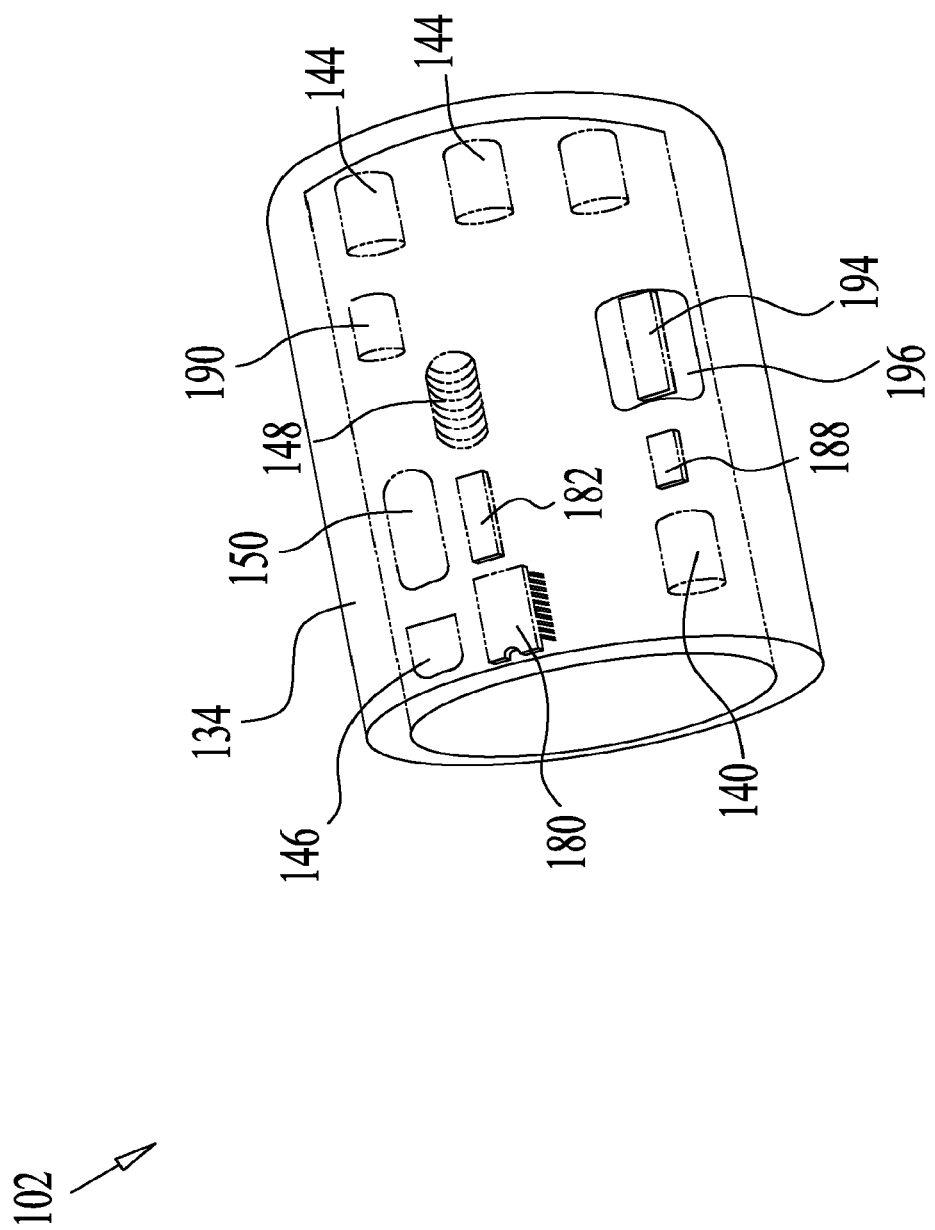
FIG. 4 is a schematic illustration of a drug dispensing-tracking device shown in FIG. 1.

In some embodiments, a plurality of microphones 144 may be provided and may be arranged around a periphery of the sleeve 134, as shown in FIG. 4 or at any other location. The auditory signal detected by the microphones 144 may indicate the rotation direction of the knob 120.

In some embodiments, the signal may be a vibration signal generated by an activity performed by the injection device 106. The sensor 140 may comprise a vibration sensor for detecting the vibrations caused by the activity of the injection device 106, such as the rotation of the knob 120 and/or the pressing of the button 116. In some embodiments, the number of clicks detected by the vibration sensor may indicate the amount of drug injected by the user. Additionally, the vibration sensor may detect the direction of the rotation of the knob 120, which as described, may correspond to addition or removal of the drug for injection thereof.

In a non-limiting example, the vibration sensor may comprise a microphone or a plurality of microphones 144.

In some embodiments, the signal may be a movement signal generated by an activity performed by the injection device 106. The sensor 140 may comprise a movement sensor for detecting the displacement caused by the activity of the injection device 106, such as the rotation of the knob 120 and/or the pressing of the button 116. In some embodiments, the number of clicks detected by the displacement sensor may indicate the amount of drug injected by the user. Additionally, the displacement sensor may detect the direction of the rotation of the knob 120, which as described, may correspond to addition or removal of the drug for injection thereof.

In some embodiments, the movement sensor may comprise a magnetic sensor or an electromagnetic sensor configured to detect an angular displacement caused by the rotation of the knob 120. An electromagnetic encoder may be provided therewith In some embodiments, the movement sensor may comprise an electromechanical sensor, an optical sensor, a microphone, a vibration sensor, an accelerometer, a rotational sensor, a combination thereof or any other suitable sensor for detecting movement of the injection device 106 or any other activity related thereto. For example, a laser diode and an optical detector may be used for detecting movement.

In some embodiments, the signal may be an optical signal generated by an activity performed by the injection device 106. The sensor 140 may comprise an optical sensor, such as a CCD which may image the display window 126. The display window 110 may display dose information set for injecting into a user, and the CCD may be configured to capture the dose information from the window 126. An optical element configured with the sleeve 134 to be arranged adjacent the display window 110 may be provided. Such an optical element may comprise one or more lenses.

In some embodiments, the tracking device 102 may comprise a coupling material provided to efficiently couple and transform the signal, such as the auditory signal, from the injection device 106 to the tracking device 102. The coupling material may comprise a sound conducting material.

In some embodiments, the tracking device 102 may include an isolating material to isolate noises and other sound sources external to the injection device 106.

In some embodiments the tracking device 102 may comprise an identifier 146 comprising any suitable component for identifying the tracking device 102 and/or the injection device 106. In a non-limiting example, the identifier may comprise an RFID sticker and/or a Subscriber Identification Module (SIM) card.

In some embodiments, the sensor 140, upon detecting the selected amount of drug, may inform the user, via a speaker 148 or by any other announcement means. This enables visually impaired insulin dependent diabetics to correctly set the injection device 106 to the correct amount.

In some embodiments, the tracking device 102 may comprise electrical components and a transmission element 150 for transmitting the detected signal or data related thereto to an external unit 154. The transmission element 150 may comprise any element configured to pass the signal from the tracking device 102 thereon. The transmission element 150 may comprise for example, a transmitter, a transponder, an antenna, a transducer, and/or an RLC circuit. The electrical components may comprise any suitable components for detecting, processing, storing and/or transmitting a signal, such as electrical circuitry, an analog-to-digital (A/D) converter, and an electrical circuit for analog or digital short range communication, for example The external unit 154 may be any apparatus configured to receive the detected signal or data related thereto for processing thereof and/or for further transmitting the detected signal or data related thereto to a central database 158. In some embodiments, the external unit 154 may comprise any one of a computer, a cellular phone, smartphone, or a tablet. In some embodiments, the external unit 154 may comprise a glucose meter. In some embodiments, the external unit 154 may comprise a treatment device 160 (FIG. 8) worn on the skin of a user to treat an injection site to improve the pharmacodynamics of the drug during a period of delivery of the drug to the user. The injection site may be an intradermal layer. The treatment device 160 may comprise a treatment device disclosed in applicant's PCT patent application PCT/IB2009/007600 or PCT/IB2012/052335, all incorporated herein by reference in their entireties and may be referred to in this disclosure as the "INSUPAD®".

The central database 158 may comprise any suitable device or function for storage of the data and/or analysis thereof. The central database may comprise a processor and/or memory. In a non-limiting example the central database 158 may comprise a computer, PC, laptop, tablet, smartphone, media player or personal data assistant ("PDA").

The drug dispensing-tracking system 100 may comprise a processor for processing the detected signal and/or data received from the tracking device 102. A memory may also be provided for storing the detected signal and/or data.

In some embodiments, the external unit 154 may comprise a processor 170. The sensor 140 may generate a second signal in response to the detected signal. The second signal may be transmitted via transmission element 150 to the external unit 154. The external unit processor 170 may process and analyze the second signal and convert it to data. The data may be transmitted to the central database 158. In such embodiments, the data may be transmitted to the central database 158 at the time the detected signal is generated, namely transmission in real-time.

In some embodiments, the data may be relayed via wireless or wired connection by the external unit 154 to the central database 158.

In some embodiments, the external unit 154 may comprise a memory 172. The data may be stored in the memory 172 and may be transmitted thereafter to the central database 158.

In some embodiments, the tracking device may comprise a processor 180. The detected signal and/or the second signal may be processed and analyzed and converted to data by the processor 180. The data may be transmitted to the external unit 154 or may be first stored in a memory 182 of the tracking device 102 and thereafter may be transmitted from the tracking device memory 182 the external unit 154. In one embodiment, the external unit 154 may transmit the data to the central database 158. In another embodiment, the data may be further processed by the injection device processor 170 and thereafter may be transmitted to the central database 158. In another embodiment, the data may be further processed by the injection device processor 170, stored in the injection device memory 172 and thereafter may be transmitted to the central database 158. In another embodiment, the data may be transmitted from the tracking device processor 180 or the tracking device memory 182 directly to the central database 158 or concurrently with transmission to the external unit 154.

In accordance with the system and method of the disclosure, the sensor 140 may be configured to detect signals in any suitable detection pattern determining the detection duration and frequency of detection in the duration. Some exemplary detection patterns may be selected as follows:

In some embodiments, the sensor 140 may be frequently or periodically sampled by the tracking device 102 processor 180 and/or external unit processor 170.

In some embodiments, the sensor 140 may be configured to detect a signal automatically, such as upon an injection event or activity and/or at predetermined time periods. The injection event may include the injection of the drug. An example of a tracking device 102 detecting a signal upon use of the injection device 106 is described in reference to FIGS. 6A-7.

In some embodiments, the sensor 140 may be configured to detect a signal automatically, such as upon a pre-injection event proceeding or anticipating the injection event. For example, the tracking device 102 may comprise an element (e.g., a sensor) configured for the automatic detection of an injection event (e.g., an injection event sensor). This element may be monitored by processor 180 via software associated therewith, to sense when an injection activity is performed. The injection event sensor may be prompted by communication between the electrical components of the tracking device 102 and electrical components of the external unit 154. For example, when the external unit 154 comprises a blood glucose meter the injection event sensor may detect a blood glucose measurement. When the external unit comprises a treatment device 160, the injection event sensor may detect activation of the treatment device 160. Since the activity of the external unit 154 (e.g. a blood glucose measurement or activation of the treatment device 160) occurs prior to the injection activity, in some embodiments, this activity may be used to signal that an injection is expected to be performed, thereby activating sensor 140. According to this embodiment, the detection occurs around the injection event, thus reducing unnecessary detection, and hence preserving the operation power of the tracking device 102. In some embodiments, the sensor 140 may be frequently or periodically sampled by the tracking device processor 180 and/or external unit processor 170.

In some embodiments, the tracking device 102 may be preset to detect at predetermined time intervals, generally when basal drug doses are injected, such as for example in the morning and/or at night.

In some embodiments, the tracking device 102 may comprise a switch 188 or a component configured to prompt the sensor 140 to detect a signal. The switch 188 may be switched on by a user or in response to any other event, such as by a signal provided by the external unit 154. For example, when the external unit 154 comprises a treatment device 160, the operation of the treatment device 160 may be used to switch on the switch 188.

In some embodiments, the switch may be positioned in, on or adjacent to the rotating element (e.g. the cap 130) of the injection device.

In some embodiments, the switch may be toggled between two or more states by the user, including, for example, a state for switching on the tracking device 102 and turning off the tracking device 102. The switch 188 may be toggled between an "off" state and an "on" state in response to any suitable trigger, such as the operation of the injection device 106 or the rotation direction of the rotation knob 120. In some embodiments, the states may comprise at least one of: a state for turning on the tracking device 102, a state indicating the direction of the injection device movement as it is set by the user to the amount of the injected drug, a state indicating re-adjustment of an amount of drug before injection, and a state indicating the drug is to be injected.

In some embodiments, the external unit 154 may comprise a switch or a component configured to detect the second signal transmitted from the tracking device 102.

In some embodiments, the external unit 154 may include a proximity detector for detecting the presence of the tracking device 102 when in proximity thereto, thereby triggering the external unit 154 to detect the second signal transmitted from the tracking device 102.

The data may comprise any data related to the activity of the injection device 106, such as the amount of injected drug, the injection time, the injection duration. The data may comprise information related to the type of drug as well as identification of the injection device 106 and/or the tracking device 102. In the treatment course of a diabetic patient, different types and/or quantities if insulin are administrated, such as a basal insulin dose and a bolus insulin dose. The different doses may be injected by different injection devices 106. Therefore, data indicating the type of injected dose assists the user, caretaker or physician in monitoring the course of correct treatment.

The data may comprise time information corresponding to the date and time of a respective injection.

In some embodiments, the tracking device 102 and or the external unit 154 may be programmed to anticipate injection of the drug at predetermined periods and with predetermined amount or dosage. Accordingly, the data may also indicate omission of an anticipated injection or incorrect dosage.

In some embodiments, the data may be used to monitor the expiration of the drug. This may be determined by measuring the time discrepancy between the first use of the injection device 106 and a current time or by comparing the date of the drug injection with an expiration date provided by the drug manufacturer.

In some embodiments, the tracking device 102 may include a temperature sensor and the data may detect the temperature of the drug and/or the ambient environment. The temperature measurement may be used to indicate overheating and hence inefficacy of the drug. In some embodiments, when the external unit comprises a treatment device 160 utilizing heat, the temperature sensor may detect the temperature of the treatment device 160 thereby ensuring the treatment device operates properly and/or possibly adapt the injection accordingly.

The detected signal, second signal and/or data may be transmitted from the tracking device 102 to the external unit 154, and to the central database 158; and/or from the tracking device 102 to the central database 158 in any suitable manner, such as wirelessly, via an analog short range communication mode, or a digital communication mode including WIFI or Bluetooth, or via a wired connection. Additional examples for transmission may be via a network. The network may comprise a local area network (LAN), a wide area network (WAN), or a global network, for example. The network may be part of, or comprise any suitable networking system, such as the Internet, for example, or an Intranet. Generally, the term "Internet" may refer to the worldwide collection of networks, gateways, routers, and computers that use Transmission Control Protocol/Internet Protocol ("TCP/IP") and other packet based protocols to communicate therebetween.

In some embodiments, such as when the sensor 140 comprises a microphone, the tracking device 102 may comprise an antenna 190 provided for wirelessly transmitting the signal.

The data may be used by a physician, caretaker or the patient to track treatment goals. The data may be used with data provided by the glucose meter. Additionally, the data may be used to alert the patient upon passage of the drug expiration date. Moreover the data may be used to alert the patient upon reduction of the efficacy of the drug due to excess heat or any other relevant parameter.

Figure 5:
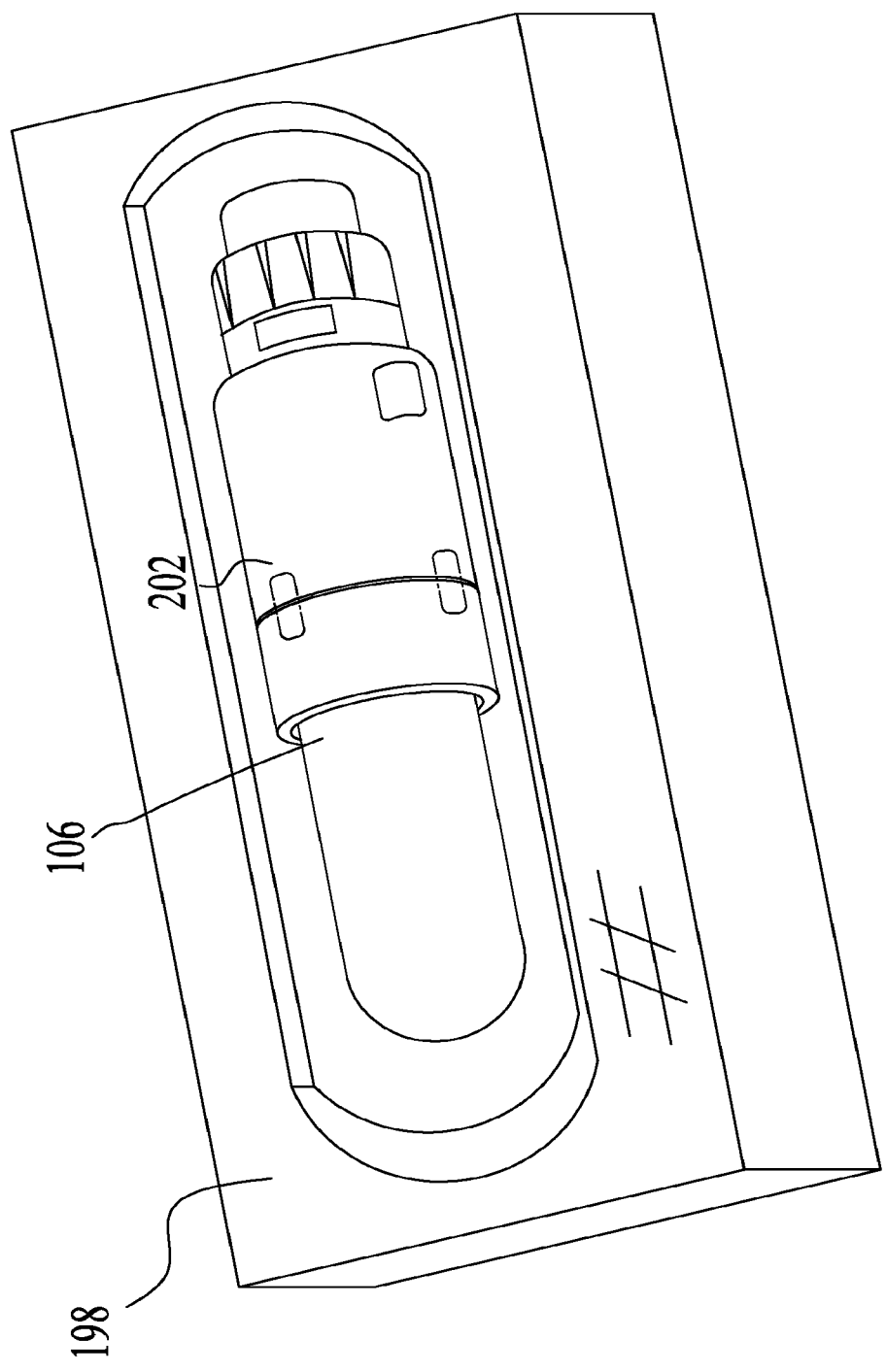
FIG. 5 is a schematic illustration of an exemplary drug dispensing-tracking system according to some embodiments of the present disclosure.

The tracking device 102 may operate using any suitable power source 192, such as, a battery 194. In some embodiments the tracking device 102 may comprise a battery enclosure 196 for removing a discharged battery 194 and replacing it with a new battery. In some embodiments, the battery 194 may be recharged by inserting the tracking device 102 (and, in some embodiments, the injection device 106) on a recharging cradle 198, as shown in FIG. 5. In another embodiment, the tracking device 102 may be connected to an electricity source via a cable.

FIGS. 6A-7 are illustrations of an exemplary drug dispensing-tracking system 100. As shown, a tracking device 202 may be formed with a first section 204 inserted on the shaft 108 and a second section 208 inserted on the cap 130. A mechanical connection, such as at least one pin 212 (FIG. 6B-7) may connect the first section 204 to the second section 208. The pins 212 may be configured to separate into two first and second portions 214 and 218, each placed on the corresponding first section 204 and the second section 208.

In some embodiments, as seen in FIG. 6A, the sleeve 134 comprises mechanical features including the perforation 138, and can be opened along its longitudinal axis 139. Mounting the sleeve 134 to the injection device 106 may be made when the cap 130 of the injection device 106 is mounted properly on the injection device 106, then by opening the sleeve 134 along its longitudinal axis 139, fitting its mechanical features to the injection device mechanical features, while the perforation 138 of the sleeve 134 is next to the area of the injection device 106 between the cap 130 and the body (e.g. the shaft 108) of the injection device 106. Closing the sleeve 134 in the orientation of arrow 222, may fix the perforation 138 where the cap 130 and body of the injection device connect, such that disconnecting the cap 130 from the injection device 106 breaks the perforation of the sleeve 134, leaving first section 204 firmly affixed to the body of the injection device and second section 208 firmly affixed to the cap 130 of the injection device, as shown in FIG. 6C.

Figure 6C:
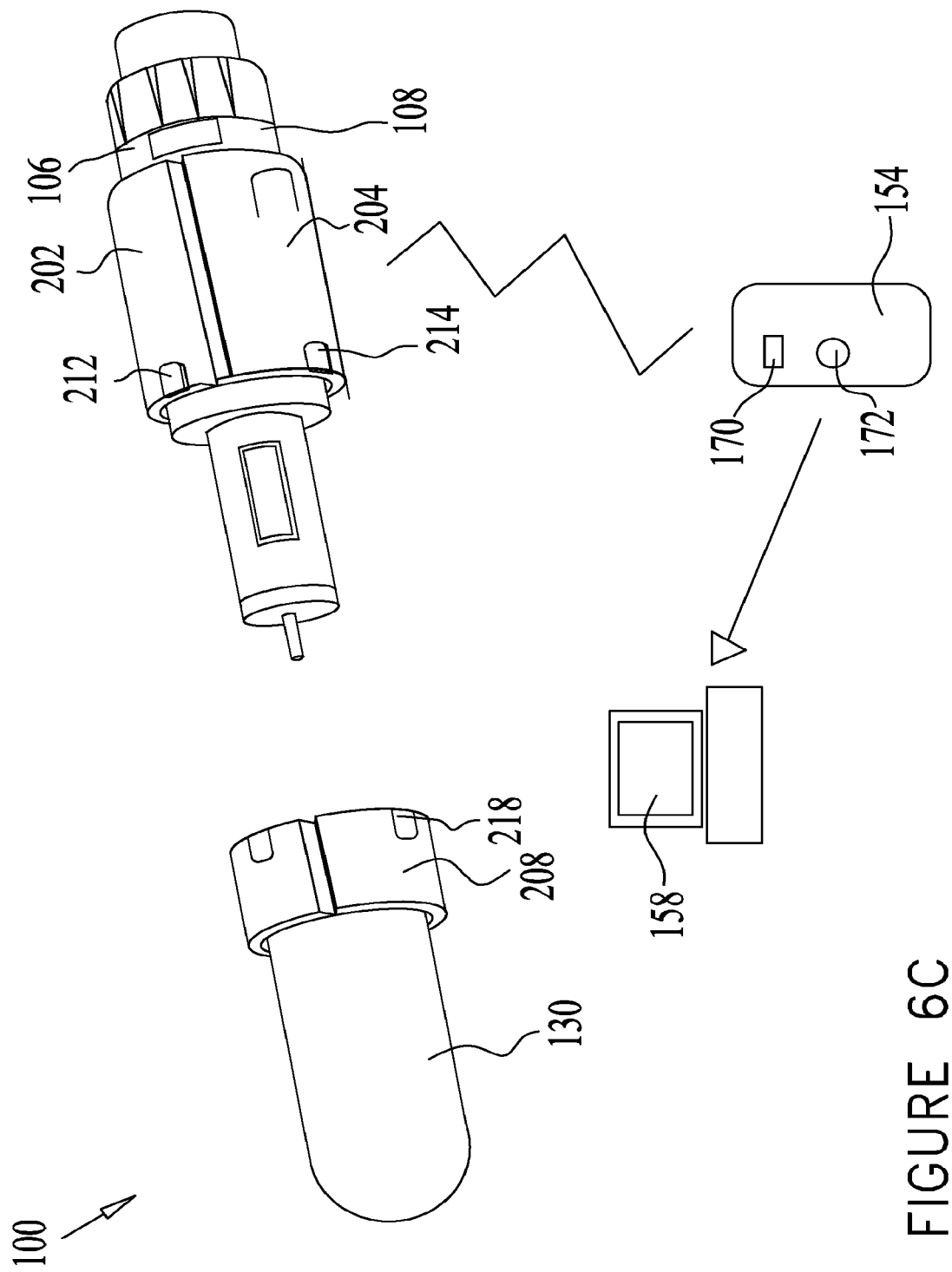

Turning to FIGS. 6B and 6C, upon removal of the cap 130 from the injection device 106, such as in prior to operating the injection device 106, the first pin portion 214 disconnects from the second portion 218. The tracking device 102 is formed such that the disconnection of the pin portions 214 from 218 triggers the sensor 140 to commence its detecting operation. Upon reinserting the cap 130 on the injection device 106 and hence reconnecting the first pin portion 214 to the second pin portion 218, the sensor operation may be terminated.

In some embodiments, the pin 212 may comprise an activation pin configured to turn on the switch 188 upon disconnection of the first portion 214 from the second portion 218 via appropriate electrical circuitry and components.

As seen in FIG. 6B, the first and second portions 214 and 218 may be connected and the sensor has yet to commence its operation. Upon removal of cap 130, the first and second portions 214 and 218 are disconnected, as seen in FIGS. 6C and 7, thereby triggering the detection operation, which may operate as described in reference to FIGS. 1-5. In this embodiment, the operating of the tracking device 102 is switched on or off in a simple manner due to the simple, mechanical operation of the pins 212.

In some embodiments, the tracking device 102, or 202, may be configured to be used with a single (disposable or multiple use) injection device 106. In some embodiments the tracking device 102 or 202 may be configured for multiple use and may be placed on a plurality of injection devices 106.

Figure 8:
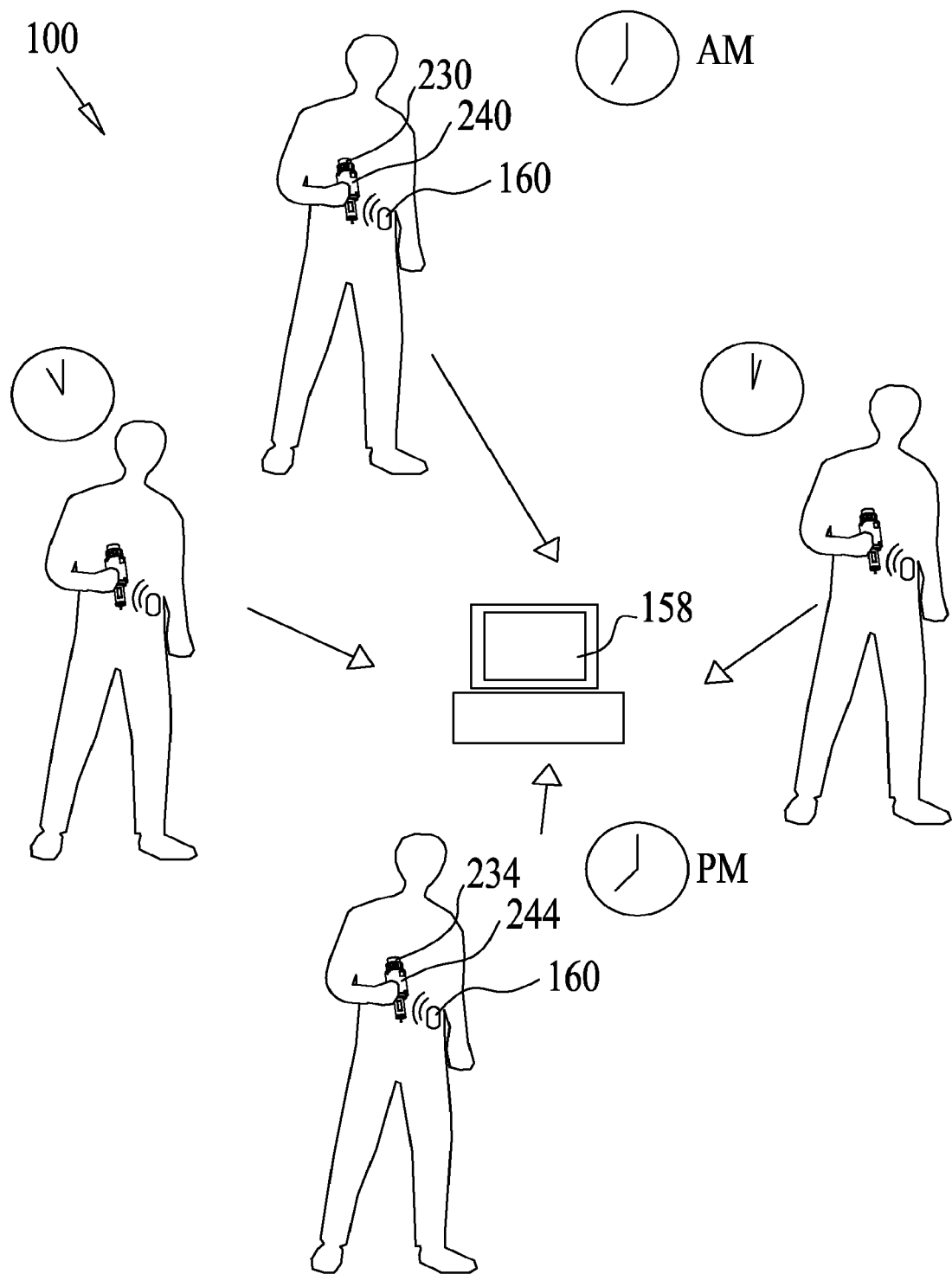
FIG. 8 is a schematic illustration of an exemplary drug dispensing-tracking system according to some embodiments of the present disclosure.

FIG. 8 is a schematic illustration of an exemplary drug dispensing-tracking system 100 according to some embodiments. As seen in FIG. 8, a user may use different injection devices during the treatment course, such as a first injection device 230 in the morning and a second injection device 234 at night.

Each injection device 106 may be designed with different mechanical, electrical and/or pharmaceutical features, as common in the commercial injection device market. Accordingly, the tracking devices 102 may be configured to fit the features of the different injection devices. For example, the injection device 106 may be formed with unique mechanical features and the tracking device 102 may be formed with corresponding mechanical features.

As described above, as each commercial injection device 106 may be configured to inject a selected drug and a selected dose, identifying the corresponding sleeve may also identify the selected drug and a selected dose. This identifying information may be transmitted to the external unit 154 and/or central database 158.

Similarly, the sensor 140 of a first tracking device 240 may be calibrated to detect an injection of a first drug or dosage by the first injection device 230. A sensor 140 of a second tracking device 244 may be calibrated to detect an injection of a second drug or dosage by the second injection device 234.

Each injection device 230 or 234 may include a unique identifier and the unique identification may be transmitted to the external unit 154, here shown as the treatment device 160.

In some embodiments, the carrier frequency of the signal from the sensor 140 may be utilized as the unique identifier of a specific type of injection device 106. The external unit 154 may include electronics with several electronic filters, at least some used to detect signals broadcasted from a different injection device 106, allowing the external unit 154 to analyze signals from different injection device 106 and record the amount of drug injected from each one of them along with time and date information or any other relevant data.

The data from the different tracking devices 240 and 244 may be transmitted via the external unit 154 (or directly) to the central database 158. Thus, in some embodiments, systems, methods and devices may collect, store and log data from a plurality of injection events and/or injection devices, which, without the tracking device according to some embodiments, would be lost.

FIG. 9 is a graph illustrating a method for tracking dispensing of a drug from the injection device 106 according to some embodiments. In FIG. 9, there is shown an exemplary algorithm for identifying the direction of rotation of an injection device 106 and, in some embodiments, counts the sum of the rotations. The algorithm may provide a sum which represents the amount of drug to be injected. FIG. 9 shows an injection event where the total rotations in the first direction is 8 (shown as the downwardly oriented signals 250) and the total rotations in the opposite direction is 2 (shown as the upwardly oriented signals 260). In a non-limiting example, rotation in the first direction indicates adding a predetermined drug amount X and rotation in the second, opposite direction indicates subtracting the predetermined drug amount X. Accordingly, the data logged on the central database 158 can indicate that the total amount of the injected drug is 8X−2X=6X.

In accordance with an embodiment, the sleeve 134 may comprise microphone 144, power source 192, switch 188, and transmission element 150, and may be attached to each injection device 106 by the user. After the user completes setting the injection device 106 to the desired amount of drug by setting the rotation knob 120 of the injection device 106, the user may use the switch 188 on the sleeve 134 to turn "on" the sleeve 134. When the injection is performed, the electronics of the sleeve 134 may wirelessly transmit by transmission methods known in the art, the sound and vibration created, to the external unit 154. The processor 170 of the external unit 154 (which can be a treatment device, such as treatment device 160) may analyze the information to find the amount of drug injected and either store the information in the external unit memory 172 for later download, or transmit the information in real-time to the central database 158.

In accordance with some embodiments, the sleeve 134 may include microphone 144, power source 192, processor 180 and a transmission element 150 comprising a transmitter. The microphone 144 may be frequently sampled by the processor 180 to analyze the sound and/or vibration created when the rotation knob 120 of the injection device 106 is turned in order to detect an injection event. When the user "sets" the injection device 106 the microphone 144 may pick up the sound and/or vibration created during the setting event. When the processor 180 analyzes that the setting event is completed, it may be configured to activate the transmitter. The sound and/or vibration created (or corresponding data associated therewith) when the drug is injected may then be transmitted wirelessly to the external unit 154. Since, the sound and vibration created when the drug is injected as the rotation knob 120 of the injection device 106 is rotated in one direction differs from those created during the setting event when the rotation knob 120 of the injection device 106 is rotated to another opposite direction, it is possible for the processor 180 on the sleeve 134 to distinguish between these two events and turn on the transmitter only before the drug is injected (thereby preserving battery power). The processor 170 of the external unit 154 may analyze the received signal/data to determine the amount of drug that was just injected.

In some embodiments, injection devices have a protective cap 130 that is removed before injection is made. Therefore, in accordance with some embodiments of the present disclosure, the sleeve electronics may be turned "on" when the cap 130 is removed. The microphone signal/data may be then transmitted wirelessly to the external unit 154 to be analyzed in order to determine the amount of drug that was just injected.

In accordance with an embodiment of the present disclosure, the tracking device 102 may be formed with a mechanical attachment to the injection device 106. The mechanical attachment can be separated to a part which fits the cap 130 (shown in FIGS. 6A-6C as second section 208) and a part (shown as first section 204) that fits the injection device body (e.g. the shaft 108). The part which fits the cap 130 may have at least one activation pin 212 extending out. These one or more activation pins 212 may contact the switch 188 inside the part of the sleeve 134 that mechanically fits the injection device body (e.g. the shaft 108). The part of the sleeve 134 that fits the injection device body may further include the electrical circuit, power source 192, microphone 144, wireless transponder and, in some embodiments, the processor 180 and memory 182. When a user removes the cap 130 to inject the drug, the activation pin 212 disconnects from the switch 188 and this turns on the electrical components of the circuit on the sleeve part which fits the injection device body. This may be configured to thereby activate the microphone 144, the transmitter and/or transponder, and in some embodiments, the processor 180, to measure the amount of drug that was injected and transmits the data to the external unit 154.

In some embodiments, the injection device 106 may be provided with wireless cellular capabilities. In such injection devices 106, with each injection the injection information may be wirelessly transmitted and logged in a central database 158 for real-time analysis and feedback to the user.

In some embodiments, the drug dispensing-tracking system 100 for capturing, transferring and logging injection event information to the central database 158 in real-time or periodically may comprise: an injection device with cellular wireless transmission capabilities, or an injector device adaptor (e.g. the tracking device 102) comprising: a mechanical attachment body (e.g. the sleeve 134) configured for mounting with (e.g., in and/or on) the injection device 106, battery 194 and electronics to sense and transmit to the external unit 154 injection information, of injections made by the injection device. The drug dispensing-tracking system 100 may further comprise external unit 154, and/or the injection device adaptor can capture, analyze, store and transmit injection information to central database 158. The external unit 154 may comprise at least one of a blood glucose meter, a treatment device 160, a cellular phone/device, and any other device in wireless communication with the injection device.

In some embodiments, several microphones 144 may be arranged in the sleeve 134, as seen in FIG. 4. In such an arrangement, when all microphones 144 are activated, the processor 180 on the sleeve, and/or the processor 170 of the external unit 154, may be configured to analyze the signal from the microphones 144 to determine the direction to which the rotation knob 120 is rotated.

In another embodiment of the present disclosure, at least one microphone 144 may be placed inside the external unit 154 to detect the sound created when the rotation knob 120 is rotated. A controller of the external unit 154 may analyze the signal from the at least one microphone 144 to determine the amount of drug that was injected by the injection device 106.

In some embodiments, the transmission of data or sound signal between the injection device electronics to the external unit 154 may be done using any of Bluetooth short range digital communication modes or an analog communication mode.

In some embodiments, external unit 154 may be set to detect a signal coming from the injection device 106 at predetermined times or following certain activity of the external unit 154. Such activity of the external unit 154 can be, for example in the case of an INSUPAD, activation of the INSUPAD just before injection, which in a certain configuration of the INSUPAD is done by opening the INSUPAD to reveal the injection window 126. In case the external unit 154 comprises a blood glucose meter, the activity can be performing a blood glucose measurement, which is usually done before injection. In the case of predetermined time intervals, they can be preset to be in the morning or night, and will be used to detect basal injections which are usually given during theses time windows.

In some embodiments, the external unit 154 may comprise a button which is pressed by the user to move the unit to a mode where it is ready to detect the signal coming from the sleeve 134.

In some embodiments, the external unit 154 may comprise a proximity detector which may detect the presence of the sleeve 134 next to it and trigger a receiver of the external unit 154 to detect the signals coming from the sleeve 134.

In some embodiments, any combination of the preceding methods can be used in order to move the external unit 154 to a mode where it is ready to detect the signals coming from the sleeve 134 and find out from that data the amount of drug that was injected.

In some embodiments, the sleeve 134 may include a coupling material in the interface between the sleeve 134 and the injection device 106 to efficiently couple the sound from the injection device 106 into the sleeve 134.

In some embodiments, an external interface of the sleeve 134 may include an isolating material on its outer face 230 to isolate noise and other sound sources from the external surrounding.

In some embodiments, the processor which analyzes the signal to determine the amount of insulin injected, may use an algorithm which detects the different impulses present in the audio signal which are associated with the different insulin units which were injected. Those sound impulses can be detected during the initial settings of the dose when rotating the cap 130 to its initial pre-injection stage. Those sound impulses can be detected during the injection step when the cap 130 is pressed and insulin is injected and a series of sound clicks is heard. Those sound impulses can be detected also from both the sound clicks during initial dose setting and during the injection event.

In some embodiments, the processor which analyzes the signal to determine the amount of insulin injected, may use a simple comparing algorithm where a train of sound impulses is compared to a train of a pre-recorded sound impulses to determine the amount of insulin injected. The memory of the processor would contain multiple sound samples for each dose which can be injected by the specific type of injection device 106, which the sleeve 134 is intended to be used with.

In some embodiments, the sleeve 134 may contain a listening element (i.e. microphone 144), processor 180 to analyze the signal and a speaker 148. The sleeve 134 detects the amount of insulin units set by the user to inject and the microphone 144 may announce to the user the amount of insulin units which the injection device 106 is set to inject. This may enable visually impaired insulin dependent diabetic subjects to correctly set their insulin injector to the correct amount.

In some embodiments, the sleeve 134 may contain a RFID sticker to identify the injection device.

Various implementations of some of embodiments disclosed, in particular at least some of the processes discussed (or portions thereof), may be realized in digital electronic circuitry, integrated circuitry, specially configured ASICs (application specific integrated circuits), computer hardware, firmware, software, and/or combinations thereof. These various implementations, such as associated with the drug dispensing-tracking system 100 and the components thereof, for example, may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions/code for a programmable processor, for example, and may be implemented in a high-level procedural and/or object-oriented programming language, and/or in assembly/machine language. As used herein, the term "machine-readable medium" refers to any computer program product, apparatus and/or device (e.g., non-transitory mediums including, for example, magnetic discs, optical disks, flash memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a LCD (liquid crystal display) monitor and the like) for displaying information to the user and a keyboard and/or a pointing device (e.g., a mouse or a trackball, touchscreen) by which the user may provide input to the computer. For example, this program can be stored, executed and operated by the dispensing unit, remote control, PC, laptop, smartphone, media player or personal data assistant ("PDA"). Other kinds of devices may be used to provide for interaction with a user as well. For example, feedback provided to the user may be any form of sensory feedback (e.g., visual feedback, auditory feedback, or tactile feedback), and input from the user may be received in any form, including acoustic, speech, or tactile input. Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components.

The components of the system may be interconnected by any form or medium of digital data communication (e.g., a communication network). Examples of communication networks include a local area network ("LAN"), a wide area network ("WAN"), and the Internet. The computing system according to some such embodiments described above may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented anywhere in the present application, are herein incorporated by reference in their entirety.

Example embodiments of the devices, systems and methods have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements/features from any other disclosed methods, systems, and devices, including any and all features corresponding to translocation control. In other words, features from one and/or another disclosed embodiment may be interchangeable with features from other disclosed embodiments, which, in turn, correspond to yet other embodiments. Furthermore, one or more features/elements of disclosed embodiments may be removed and still result in patentable subject matter (and thus, resulting in yet more embodiments of the subject disclosure).

What is claimed is:

1. An injector device adaptor for use in combination with a drug injection device, which drug injection device is formed with a: rotation knob for setting a drug dose to be injected, a display window, and a button for injecting the set dose upon pressing the button, the injector device adaptor comprising:

a removable mechanical attachment body configured for mounting the injector device adaptor on the drug injection device;

at least one optical sensor configured to image the display window, thereby generating an optical signal, the optical sensor being positioned adjacent the display window while not obstructing the display window from view of a user while the removable mechanical attachment body is mounted on the drug injection device, and wherein the injector device adaptor is positioned such that the button is unobstructed and is pressable by the user via direct contact with the user's hand, and the rotation knob is unobstructed and is rotatable by the user via direct contact with the user's hand;

a vibration sensor comprising an accelerometer configured to detect a vibration signal generated by at least one of: the rotation of the rotation knob and the pressing of the button;

a processor for processing at least one of the optical signal, and vibration signal and converting the at least one of the optical signal, and vibration signal to data; and a transmission element for transmitting at least one of the optical signal and vibration signal and the converted data to an external unit.

2. The injector device adaptor according to claim 1, further comprising a unique identifier.

3. The injector device adaptor according to claim 2, wherein several different injector device adaptors are provided, each with a unique identifier, and wherein the external device is configured to detect a signal based on the unique identifier, thereby identifying each of the different injector device adaptors.

4. The injector device adaptor according to claim 1, further comprising a unique identifier including a unique carrier frequency.

5. The injector device adaptor according to claim 1, and further comprising a coupling material comprising a vibration conducting material for transforming the vibration signal from the drug injection device to the vibration sensor.

6. The injector device adaptor according to claim 1 wherein the external unit comprises a proximity detector for detecting a presence of the injector device adaptor, the proximity detector being configured to perform at least one of:
 upon detection of the injector device adaptor being in proximity to the external unit, to trigger the external unit to detect any one of the optical signal, and vibration signal; and
 upon detection of the injector device adaptor being out of proximity to the external unit, to generate an alert.

7. The injector device adaptor according claim 1, wherein imaging the display window is performed by the optical sensor comprising a CCD and an optical element comprising one or more lenses.

8. The injector device adaptor according to claim 1, wherein the rotation of the rotation knob produces a vibration upon rotation thereof, wherein rotation of the rotation knob in a first direction increases the set dose to be injected and rotation of the rotation knob in a second, opposite direction reduces the set dose to be injected,
 the vibration sensor is configured to detect a vibration signal generated by rotation of the rotation knob in the first and second direction; and
 wherein the processor having computer instructions operating thereon is configured to cause the processor to:
  distinguish between the vibration signal generated by rotation of the rotation knob in the first direction and the vibration signal generated by rotation of the rotation knob in the second direction;
  count a number of rotations of the rotation knob in the first direction and a number of rotations in the second direction; and
  subtract the number of rotations in the second direction from the number of rotations in the first direction so as to calculate the set dose to be injected.

9. The injector device adaptor according to claim 1, wherein the injector device adaptor comprises a memory, and wherein the processor has computer instructions operating thereon configured to cause the processor to analyze a signal response of the vibration signal by comparing a train of received signal responses of the vibration signal with pre-recorded impulses stored in the memory.

10. The injector device adaptor according to claim 1, wherein the external unit is selected from the group consisting of: a glucose meter, a computer, a smartphone, a tablet, and a treatment device worn on the skin of the user to treat an injection site to improve pharmacodynamics of the drug during a period of delivery of the drug to the user.

11. The injector device adaptor according to claim 1, wherein the drug injection device includes a cap and the body is configured with two sections connected together before and at a time of placement of the injector device adaptor on the drug injection device, and wherein upon removal of the cap from the drug injection device, the two sections are separated resulting in two separate sections.

12. The injector device adaptor according to claim 11, wherein each of the two sections of the body is provided with at least a portion of a pin and the at least a portion of the pin is configured to operate a switch.

13. The injector device adaptor according to claim 11, wherein separation of the two sections is such that their removal from the drug injection device results in two separate parts which are thereafter incapable of being connected together.

14. The injector device adaptor according to claim 1, wherein the external unit and/or the processor is configured to receive the converted data from at least one of the optical signal and vibration signal and analyze the data to determine the amount of drug injected.

15. The injector device adaptor according to claim 1, wherein the external unit includes a memory, and the data is stored in the memory.

16. The injector device adaptor according to claim 1, wherein the data is stored in a memory along with time information corresponding to at least one of a date and time of a respective injection.

17. An injector device adaptor used with a drug injection device, which drug injection device is formed with a: rotation knob for setting a drug dose to be injected, a display window, and a button for injecting the set dose upon pressing the button, the injector device adaptor comprising:
 a removable mechanical attachment body configured for mounting the injector device adaptor on the drug injection device;
 an optical sensor configured to image the display window, thereby generating an optical signal, the optical sensor being positioned adjacent the display window while not obstructing the display window from view of a user while the removable mechanical attachment body is mounted on the drug injection device, and wherein the injector device adaptor is positioned such that the button is unobstructed and is pressable by the user via direct contact with the user's hand, and the rotation knob is unobstructed and is rotatable by the user via direct contact with the user's hand;
 a vibration sensor comprising an accelerometer configured to detect a vibration signal generated by at least one of: the rotation of the rotation knob and the pressing of the button;
 a temperature sensor configured to detect a temperature of the drug, thereby generating a temperature signal;
 a processor for processing at least one of the optical signal and vibration signal and temperature signal and converting the at least one of the optical signal and vibration signal and temperature signal to data; and
 a transmission element for transmitting at least one of the optical signal, vibration signal and temperature signal and the converted data to an external unit.

18. A method for tracking dispensing of a drug from a drug injection device formed with a rotation knob for setting a drug dose to be injected, a display window, and a button for injecting the set dose upon pressing the button, the method comprising:
 mounting an injector device adaptor on the drug injection device, wherein the injector device adaptor is positioned on the drug injection device such that the button is unobstructed and is pressable by a user via direct contact with the user's hand, and the rotation knob is unobstructed and is rotatable by the user via direct contact with the user's hand;

the injector device adaptor comprising a removable mechanical attachment body, at least one optical sensor, a vibration sensor, a processor and a transmission element;

imaging the display window by the optical sensor whereupon the optical sensor is positioned adjacent the display window while not obstructing the display window from view of the user while the removable mechanical attachment body is mounted on the drug injection device;

detecting a vibration signal generated by at least one of: the rotation of the rotation knob and the pressing of the button;

converting by the processor the at least one of the image and the vibration signal to data;

transmitting by the transmission element at least one of the optical signal, vibration signal and the converted data to an external unit, wherein at least one or more of the: image, rotation of the rotation knob and the pressing of the button are indicative of the amount of drug injected by the drug injection device.

19. The method according to claim 18, wherein the injector device adaptor further comprises a switch that can be toggled between two or more states, and wherein the method further comprises switching the switch to one state of the two or more states.

20. The method according to claim 19, wherein the two or more states comprise at least two of: a state for turning on the drug injection device, a state indicating re-adjustment of an amount of drug before injection, a state indicating the drug is to be injected.

* * * * *